United States Patent

Ueda et al.

[11] Patent Number: 5,228,898
[45] Date of Patent: Jul. 20, 1993

[54] SUBSTITUTED BICYCLOHEPTANDIONE DERIVATIVES

[75] Inventors: Akiyoshi Ueda, Odawara; Shigemi Suga, Takaoka; Hiroyuki Adachi, Odawara; Toshio Aihara, Hiratsuka; Kazuyuki Tomida, Odawara; Hideki Yamagishi, Shizuoka; Hideo Hosaka, Odawara, all of Japan

[73] Assignee: Nippon Soda Co., Ltd., Tokyo, Japan

[21] Appl. No.: 651,266

[22] PCT Filed: Jun. 29, 1990

[86] PCT No.: PCT/JP90/00850
§ 371 Date: Feb. 3, 1992
§ 102(e) Date: Feb. 3, 1993

[87] PCT Pub. No.: WO91/00260
PCT Pub. Date: Jan. 10, 1991

[30] Foreign Application Priority Data

Jul. 4, 1989 [JP] Japan .................. 1-172423
Aug. 10, 1989 [JP] Japan .................. 1-207501
Oct. 3, 1989 [JP] Japan .................. 1-257157
Jan. 11, 1990 [JP] Japan .................. 2-3854

[51] Int. Cl.$^5$ .................. A01N 43/00; A01N 41/00; A01N 31/00; C07C 313/00; C07C 61/12; C07C 69/74; C07C 321/00

[52] U.S. Cl. .................. 504/348; 504/178; 504/174; 504/181; 504/182; 504/183; 504/309; 504/315; 504/256; 504/314; 504/260; 504/255; 504/239; 504/242; 504/243; 504/266; 504/280; 504/313; 504/326; 504/316; 504/339; 544/309; 544/311; 544/319; 544/355; 546/314; 546/315; 548/200; 548/530; 548/539; 558/45; 558/57; 558/61; 558/62; 558/193; 558/198; 558/209; 558/214; 558/386; 558/414; 560/117; 560/119; 562/499; 562/500; 562/502; 564/162; 564/169; 564/308; 568/376

[58] Field of Search .............. 544/335, 309, 311, 319; 546/315, 314; 548/200, 530, 539; 568/376; 71/92, 94, 95, 90, 79, 113, 103, 105, 107, 114, 115, 118, 121, 122, 123, 86, 87; 558/45, 57, 61, 62, 193, 198, 209, 214, 386, 414; 560/117, 119; 562/499, 502, 500; 564/162, 169, 308

[56] References Cited

U.S. PATENT DOCUMENTS 4,921,526 5/1990 Lee et al. .................. 71/86

FOREIGN PATENT DOCUMENTS 137963 4/1985 European Pat. Off. .
264737 4/1988 European Pat. Off. .
3902818 8/1989 Fed. Rep. of Germany .

OTHER PUBLICATIONS

March, Advanced Organic Chemistry, 3rd Edition 1985, p. 414.

Primary Examiner—Cecilia Tsang
Attorney, Agent, or Firm—Joseph C. Mason, Jr.; Ronald E. Smith

[57] ABSTRACT

This invention relates to substituted bicycloheptadione derivatives with high herbicidal activity which are represented by general formula (I)

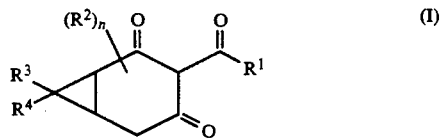

(where $R^1$ is a lower alkyl group, a phenyl group which may be substituted, an aralkyl group which may be substituted, or a heterocyclic group which may be substituted;

$R^2$ is, same or different, a halogen, an alkoxy group, an alkylthio group, an alkylsulfonyl group, an alkyl group, an alkoxyalkyl group, or an alkoxycarbonyl group, and n is 0 to 4;

$R^3$ and $R^4$ are, same or different, hydrogen or a lower alkyl group).

7 Claims, No Drawings

SUBSTITUTED BICYCLOHEPTANDIONE DERIVATIVES

DESCRIPTION

1. Technical Field:

This invention relates to new substituted bicycloheptandione derivatives, their preparation methods and herbicides containing the said derivatives as effective components.

2. Background Art:

In many cases of agricultural or horticultural cultivation, a lot of kinds and amount of herbicides have come to be used for the weed control in order to save the labors consuming for removing weeds in the fields, however, in some occasion, phytotoxicity of herbicides may injure crops, or herbicides remaining in the field may cause environmental pollution.

Consequently, chemicals possessing the excellent efficacy and the higher safety to mammal have been awaited to be developed.

Known patents disclosing compounds analogous to the compounds of this invention include EP-137963, EP-135191, EP-186118, EP-186119, EP-186120, Japanese open patent No. Sho 62-123145, EP-278907, EP-268795 and EP-264737.

The compounds of this invention are included in the claims of DE 3902818 (Corresponding to GB 2215333 and Japanese open patent No. Hei 2-1422). There are no descriptions on the compounds of this invention in the Description.

An object of this invention is to provide herbicides which are synthesized advantageously in an industrial scale, have certain efficacy at a lower dosage, are very safe and have well selectivity to crops.

DISCLOSURE OF INVENTION

This invention is substituted bicycloheptandione derivatives having the formula (I)

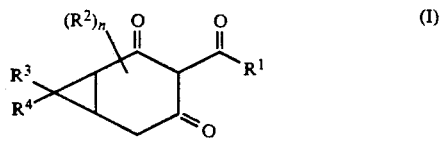

(where $R^1$ is a lower alkyl group, a phenyl group which may be substituted, an aralkyl group which may be substituted, or a heterocyclic group which may be substituted;

$R^2$ is, same or different, a halogen, an alkoxy group, an alkylthio group, an alkylsulfonyl group, an alkyl group, an alkoxyalkyl group, or an alkoxycarbonyl group, and n is 0 to 4;

$R^3$ and $R^4$ are, same or different, hydrogen or a lower alkyl group), or their salts.

The said substituents of the phenyl, aralkyl and heterocyclic groups of $R^1$ are, same or different, halogen, hydroxy, nitro, cyano, alkyl, alkenyl, haloalkyl, haloalkenyl, alkoxy, haloalkoxy, haloalkenyloxy, alkylthio, alkenylthio, alkynylthio, haloalkylthio, haloalkenylthio, monoalkylamino, dialkylamino, alkoxyalkylthio, alkylthioalkylthio, alkoxycarbonyl, alkylcarbonylalkoxy, alkylcarbonyl, alkoxyamino, alkylsulfonyl, alkenylsulfonyl, alkynylsulfonyl, alkoxyalkylsulfonyl, alkylthioalkylsulfonyl, alkylsulfonylalkylsulfonyl, haloalkylsulfonyl, alkoxycarbonylalkylthio, alkoxycarbonylalkylsulfinyl alkoxycarbonylalkylsulfonyl, alkylamido, and aralkyloxy a phenyl group which may be substituted, an aralkyl group which may be substituted, a heterocyclic group which may be substituted, and an alkyl group substituted by a heterocyclic group which may be substituted.

The said heterocyclic group includes groups of pyridyl, pyrimidyl, thienyl, furyl, pyrazolyl, pyrrolyl, imidazolyl, pyridazinyl, pyrazinyl, indolyl and others.

The compounds of this invention exhibit high herbicidal activity under upland conditions by either method of soil treatment or plat foliage treatment. It is very efficacious against various kinds of upland weeds such as crabgrass, rice flatsedge velvetheaf and redroot pigweed, in a treatment of spraying it directly on the foliage of plant in particular. Same of these compounds have selectivity to crops such as wheat and soy beans.

Some of these compounds show plant growth retardent activity on crops, ornamental pot plants and fruit trees.

Some compounds also exhibit high selectivity on rice plant and high herbicidal activity against barnyard grass, smallflower unbrellaplant, arrowhead and Japanese bulrush, etc.

In addition to the above, the compounds of this invention can be applied for weed control to such places as orchards, lawn, railroad sides and vacant lots, etc.

BEST MODE FOR CARRYING OUT THE INVENTION

The compounds of this invention are prepared by the following methods.

Preparation Method (a)

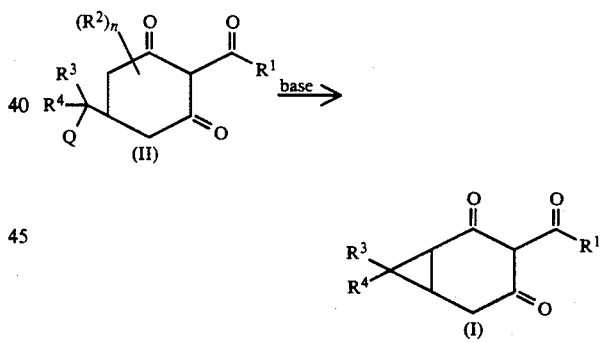

(where $R^1$, $R^2$, $R^3$, $R^4$, and n are as defined above, and Q is a leaving group).

In the process, Compound (I) is obtained in a way that Compound (II) is reacted in a solvent in the presence of 2 moles or an excessive amount of base at a temperature from $-20°$ C. to the boiling point of the solvent used, preferably $0°$ C. to $50°$ C., for 30 minutes to several 10 hours.

The leaving group of Q includes halogen, alkylsulfonate and phenylsulfonate. Bases used include alkali metal hydroxides such as KOH and NaOH, hydroxides of alkaline earth metals, tri ($C_1$-$C_6$ alkyl) amine, pyridine, DBU, t-BuOK, Triton B, sodium carbonate, sodium phosphate or the like. Solvents used include water, alcohol, methylene chloride, benzene, toluene, ethyl acetate, dimethylformamide, THF, dimethoxyethane, acetonitrile or the like.

Preparation Method (b)

Mono-substituted compounds, among the compounds of this invention, except those of which an alkoxycarbonyl group is at the 5 position of the bicyclo ring, may be prepared according to the following reaction.

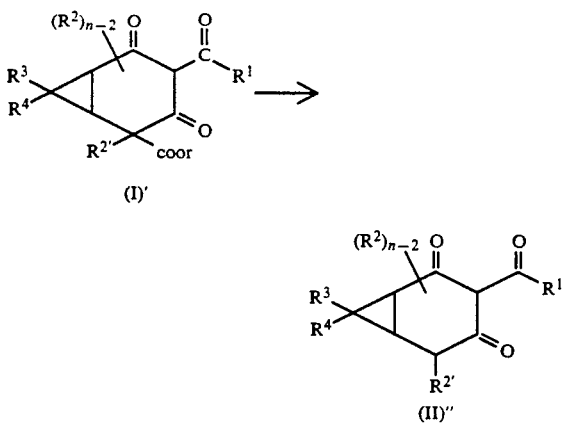

(where r is an alkyl group).

If these compounds have different substituents at the 5 positions such as (I)' or one substituent at the 5 position such as (I)'', stereoisomers exist with respect to the cyclopropane ring.

When [I]'' is directly produced according to the above-described Preparation Method (a), the trans form is usually produced. In the preparation method, it is possible to separate cis and trans forms at the stage of [I]'. An appropriate selection of the methods allows to prepare the trans or cis form of [I]''.

The material compound and the compound [I] of this invention have optical isomers, and a large number of tautomers can exist in the form of

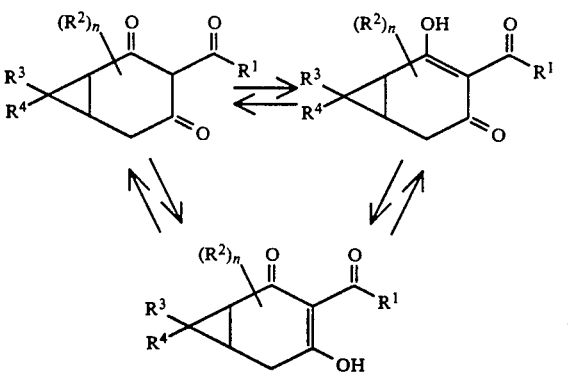

(where $R^1$, $R^2$, $R^3$, $R^4$ and n are as defined above). The compounds of such forms are all included in this invention.

If Compound [I] contains a free hydroxyl group when prepared by the above-described method, salts of the said compound, salts allowed particularly agriculturally and horticulturally, enamines and their analogues, acrylate, sulfonate, carbamate or ether can be derived from the said compound.

Appropriate salts allowed agriculturally and horticulturally include salts of sodium, potassium, calcium, ammonium or the like.

Examples of ammonium salts are salts with ion represented by formula $N^+R^aR^bR^cR^d$ (where $R^a$, $R^b$, $R^c$ and $R^d$ are respectively selected from hydrogen and $C_{1-10}$ alkyl groups substituted by, for instance, hydroxy group for some cases). If any of $R^a$, $R^b$, $R^c$ and $R^d$ are substituted alkyl groups in some cases, it is desirable that the group has 1 to 4 carbon atoms.

Appropriate enamines and their analogues are compounds of which their OH groups are respectively converted to a group represented by formula $-NR^eR^f$ (where $R^e$ is for instance an alkyl or aryl group having 1 to 6 carbon atoms and which may be substituted in some cases, or for instance a phenyl group, and $R^f$ is hydrogen, or for instance an alkyl or aryl group having 1 to 6 carbon atoms and which may be substituted in some cases, or for instance a phenyl group), halogen or $SR^g$. (Where $R^g$ is the same group as the above-described group $R^e$)

Appropriate acrylate or ether derivatives are compounds of which their OH groups are respectively converted to a group represented by formula $-OCOR^h$ or $-OR^h$ (where $R^h$ is the same group as the above-described group $R^e$).

Appropriate carbamate derivatives are compounds of which their OH groups are converted to a group represented by formula $-OC(O)NR^iR^j$ (where $R^i$ and $R^j$ are respectively hydrogen or the same as the above-described $R^e$).

These derivatives can be prepared by usual methods.

The structure of the compounds of this invention are determined by such means as IR, NMR and MS.

This invention is further described in detail by reference to the following examples.

EXAMPLE 1

3-(2-nitro-4-chlorobenzoyl) bicyclo[4,1,0]heptane-2,4-dione (Compound I-97)

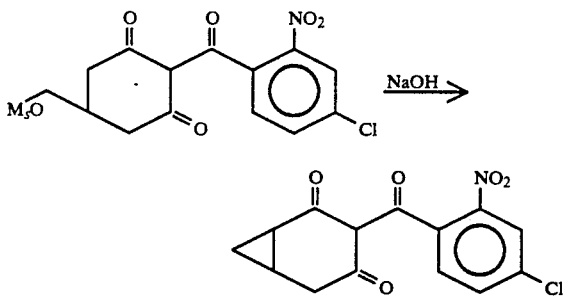

0.5 g (1.44 mmol) of 5-mesyloxymethyl-2-(2-nitro-4-chlorobenzoyl)cyclohexane-1,3-dione was dissolved in 15 ml of ethanol, to which 2 ml of aqueous solution of sodium hydroxide (sodium hydroxide: 0.17 g, 4.31 mmol) was added with stirring at room temperature and resulting mixtures stirred at room temperature for another 2 hours. After the reactin was completed, the solvent was distilled. To the obtained residue were added 50 ml of ethyl acetate and 10 ml of water to dissolve it. Dilute hydrochloric acid was added until the aqueous layer became acidic. The organic layer was washed with saturated salt water and dried with magnesium sulfate. The solvent was distilled. The obtained residue was purified with silica gel column chromatography (eluate:chloroform) to give 0.38 g (yield: 86%) of the intended product of light yellow crystal. m.p. 132°-134° C.

EXAMPLE 2

3-(2-chloro-4-methylsulfonyl-3-methoxybenzoyl)-cis-5-methyl-cis-bicyclo[4,1,0]heptane-2,4-dione (Compound I-195)

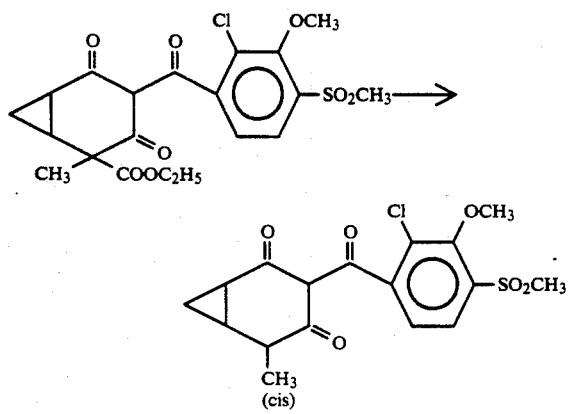

1.19 g (2.6 mmol) of 3-(2-chloro-4-methanesulfonyl-3-methoxybenzoyl)-trans-5-ethoxycarbonyl-cis-5-methyl-cis-bicyclo[4,1,0]heptane-2,4-dione was dissolved in 7.8 ml (7.8 mmol) of 1N-NaOH while cooling with ice water, then reacted at room temperature for 4 hours. After the reaction was completed, 20 ml of ice water and 20 ml of ethyl acetate were added, neutralized with 1N-HCl while cooling with ice water, and decarboxylated. The organic layer was washed with water and then with saturated salt water, and dried with MgSO4. The solvent was distilled. The residue was purified with column chromatography (benzene:ethyl acetate=5:1) to give 0.29 g of the intended product of white crystal. m.p. 132°–135° C. The obtained cis form and the trans form synthesized in the same manner as that used in Example 1 were characterized with NMR.

Representative examples of the compounds of this invention, including those obtained in the above examples, are shown in Tables 1 to 3.

Rx, Ry and Rz are the following substituents respectively in the tables. The trans and cis in the column of physical property are steric configurations of the substituent at the 5 position of the bicyclo ring and the cyclopropane ring.

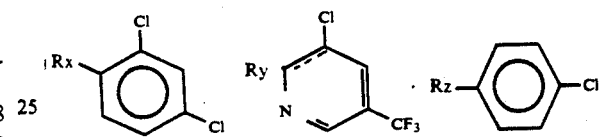

TABLE 1

Structural Formula

| No. | (R2)n | R3 | R4 | Xm | Physical Properties |
|---|---|---|---|---|---|
| I-1 | —(n = 0) | H | H | H | |
| I-2 | — | H | H | 2-Br-3-OCH3-4-OCH3 | |
| I-3 | — | H | H | 2-C2H5-4-SO2CH3 | |
| I-4 | — | H | H | 2-CF3 | |
| I-5 | — | H | H | 2-CF3-4-CF3 | |
| I-6 | — | H | H | 2-CF3-4-Cl | |
| I-7 | — | H | H | 2-CF3-4-SO2CH3 | |
| I-8 | — | H | H | 2-CH3 | |
| I-9 | — | H | H | 2-CH3-3-CH2-CH3-4-SO2CH3 | |
| I-10 | 5-CH3 | H | H | 2-CH3-3-CH2OCH3-4-SO2CH3 | mp 128–130(trans) |
| I-11 | 1-CH3 | H | H | 2-CH3-3-CH2OCH3-4-SO2CH3 | |
| I-12 | 5,5-(CH3)2 | H | H | 2-CH3-3-CH2OCH3-4-SO2CH3 | |
| I-13 | 1,5,5-(CH3)3 | H | H | 2-CH3-3-CH2OCH3-4-SO2CH3 | |
| I-14 | —(n = 0) | CH3 | CH3 | 2-CH3-3-CH2OCH3-4-SO2CH3 | |
| I-15 | — | H | H | 2-CH3-3-CH2SCH3-4-SO2CH3 | |
| I-16 | — | H | H | 2-CH3-3-CH2SO2CH3-4-SO2CH3 | |
| I-17 | — | H | H | 2-CH3-3-CH3-4-CF3 | |
| I-18 | — | H | H | 2-CH3-3-CH3-4-Cl | |
| I-19 | — | H | H | 2-CH3-3-CH3-4-SO2C3H7 (i) | |
| I-20 | — | H | H | 2-CH3-3-CH3-4-SO2CH3 | powder |
| I-21 | 5-CH3 | H | H | 2-CH3-3-CH3-4-SO2CH3 | mp 178–180(trans) |
| I-22 | 1-CH3 | H | H | 2-CH3-3-CH3-4-SO2CH3 | |
| I-23 | 5,5-(CH3)2 | H | H | 2-CH3-3-CH3-4-SO2CH3 | |
| I-24 | 1,5,5-(CH3)3 | H | H | 2-CH3-3-CH3-4-SO2CH3 | |
| I-25 | —(n = 0) | H | H | 2-CH3-3-CH3-4-SO2CH3 | |
| I-26 | — | H | H | 2-CH3-3-Cl-4-Cl | |
| I-27 | — | H | H | 2-CH3-3-Cl-4-OCH3 | |
| I-28 | — | H | H | 2-CH3-3-Cl-4-SCH3 | |
| I-29 | — | H | H | 2-CH3-3-Cl-4-SO2C3H7(i) | |
| I-30 | — | H | H | 2-CH3-3-Cl-4-SO2CH3 | |
| I-31 | —(n = 0) | H | H | 2-CH3-3-Cl-4-SOCH3 | |
| I-32 | — | H | H | 2-CH3-4-CN | |
| I-33 | — | H | H | 2-CH3-4-SCH2OCH3 | |
| I-34 | — | H | H | 2-CH3-4-SO2C3H7 (i) | |
| I-35 | — | H | H | 2-CH3-4-SO2CH3 | mp 151-3 |
| I-36 | 5-CH3 | H | H | 2-CH3-4-SO2CH3 | mp 178-8(trans) |
| I-37 | 1-CH3 | H | H | 2-CH3-4-SO2CH3 | |
| I-38 | 5,5-(CH3)2 | H | H | 2-CH3-4-SO2CH3 | |
| I-39 | 1,5,5-(CH3)3 | H | H | 2-CH3-4-SO2CH3 | |
| I-40 | —(n = 0) | CH3 | CH3 | 2-CH3-4-SO2CH3 | |
| I-41 | — | H | H | 2-Cl | |
| I-42 | — | H | H | 2-Cl-3-CH3-4-Cl | |

TABLE 1-continued

Structural Formula

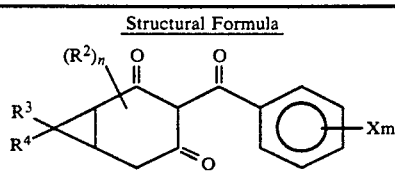

| No. | (R2)n | R3 | R4 | Xm | Physical Properties |
|---|---|---|---|---|---|
| I-43 | — | H | H | 2-Cl-3-CH3-4-SO2C3H7 (i) | |
| I-44 | — | H | H | 2-Cl-3-CH3-4-SO2CH3 | |
| I-45 | — | H | H | 2-Cl-3-Cl-4-Cl | |
| I-46 | — | H | H | 2-Cl-3-Cl-4-SO2C2H5 | |
| I-47 | — | H | H | 2-Cl-3-Cl-4-SO2C3H7 (i) | |
| I-48 | — | H | H | 2-Cl-3-Cl-4-SO2CH3 | mp 177–180(dec) |
| I-49 | 5-CH3 | H | H | 2-Cl-3-Cl-4-SO2CH3 | mp 125–7(trans) |
| I-50 | 1-CH3 | H | H | 2-Cl-3-Cl-4-SO2CH3 | powder |
| I-51 | 5,5-(CH3)2 | H | H | 2-Cl-3-Cl-4-SO2CH3 | |
| I-52 | 1,5,5-(CH3)3 | H | H | 2-Cl-3-Cl-4-SO2CH3 | |
| I-53 | —(n = 0) | CH3 | CH3 | 2-Cl-3-Cl-4-SO2CH3 | |
| I-54 | — | H | H | 2-Cl-3-OCH3-4-SO2CH3 | mp 157–8 |
| I-55 | 5-CH3 | H | H | 2-Cl-3-OCH3-4-SO2CH3 | mp 154–6(trans) |
| I-56 | 1-CH3 | H | H | 2-Cl-3-OCH3-4-SO2CH3 | oil |
| I-57 | 5,5-(CH3)2 | H | H | 2-Cl-3-OCH3-4-SO2CH3 | powder |
| I-58 | 1,5,5-(CH3)3 | H | H | 2-Cl-3-OCH3-4-SO2CH3 | |
| I-59 | —(n = 0) | CH3 | CH3 | 2-Cl-3-OCH3-4-SO2CH3 | |
| I-60 | — | H | H | 2-Cl-3-SO2CH3-4-SO2CH3 | |
| I-61 | —(n = 0) | H | H | 2-Cl-4-Cl | mp 97–8 |
| I-62 | — | H | H | 2-Cl-4-NO2 | |
| I-63 | — | H | H | 2-Cl-4-OCH3 | |
| I-64 | — | H | H | 2-Cl-4-SO2C3H7(i) | |
| I-65 | — | H | H | 2-Cl-4-SO2CH3 | mp 146–8 |
| I-66 | — | H | H | 2-CN | |
| I-67 | — | H | H | 2-COOCH3 | |
| I-68 | — | H | H | 2-COOH | |
| I-69 | — | H | H | 2-I | |
| I-70 | — | H | H | 2-NO2 | |
| I-71 | 5-CH3 | H | H | 2-NO2 | |
| I-72 | 1-CH3 | H | H | 2-NO2 | |
| I-73 | —(n = 0) | H | H | 2-NO2-3-CH2OCH3-4-SO2CH3 | |
| I-74 | — | H | H | 2-NO2-3-CH3-4-Cl | |
| I-75 | — | H | H | 2-NO2-3-CH3-4-SO2CH3 | |
| I-76 | — | H | H | 2-NO2-3-Cl-4-Cl | |
| I-77 | — | H | H | 2-NO2-3-Cl-4-SCH3 | |
| I-78 | — | H | H | 2-NO2-3-Cl-4-SO2C2H5 | |
| I-79 | — | H | H | 2-NO2-3-Cl-4-SO2CH3 | |
| I-80 | — | H | H | 2-NO2-3-OCH3-4-CH3 | |
| I-81 | — | H | H | 2-NO2-3-OCH3-4-Cl | mp 120–1 |
| I-82 | — | H | H | 2-NO2-3-OCH3-4-OCH3 | |
| I-83 | — | H | H | 2-NO2-3-OCH3-4-SO2CH3 | |
| I-84 | — | H | H | 2-NO2-3-SO2CH3-4-SO2CH3 | |
| I-85 | — | H | H | 2-NO2-4-CF3 | powder |
| I-86 | 5-CH3 | H | H | 2-NO2-4-CF3 | mp 131–4(trans) |
| I-87 | 1-CH3 | H | H | 2-NO2-4-CF3 | |
| I-88 | 5,5-(CH3)2 | H | H | 2-NO2-4-CF3 | |
| I-89 | 1,5,5-(CH3)3 | H | H | 2-NO2-4-CF3 | |
| I-90 | —(n = 0) | CH3 | CH3 | 2-NO2-4-CF3 | |
| I-91 | —(n = 0) | H | H | 2-NO2-4-CH2OCH3 | |
| I-92 | 5-CH3 | H | H | 2-NO2-4-CH2OCH3 | |
| I-93 | 1-CH3 | H | H | 2-NO2-4-CH2OCH3 | |
| I-94 | —(n = 0) | H | H | 2-NO2-4-CH3 | mp 122–4 |
| I-95 | 5-CH3 | H | H | 2-NO2-4-CH3 | |
| I-96 | 1-CH3 | H | H | 2-NO2-4-CH3 | |
| I-97 | —(n = 0) | H | H | 2-NO2-4-Cl | mp 132–4 |
| I-98 | 5-CH3 | H | H | 2-NO2-4-Cl | mp 139–141(trans) |
| I-99 | 1-CH3 | H | H | 2-NO2-4-Cl | mp 77–9 |
| I-100 | 5,5-(CH3)2 | H | H | 2-NO2-4-Cl | mp 134–5.5 |
| I-101 | 1,5,5-(CH3)3 | H | H | 2-NO2-4-Cl | powder |
| I-102 | —(n = 0) | CH3 | CH3 | 2-NO2-4-Cl | |
| I-103 | — | H | H | 2-NO2-4-CN | |
| I-104 | — | H | H | 2-NO2-4-NHCOCH3 | |
| I-105 | — | H | H | 2-NO2-4-NO2 | |
| I-106 | — | H | H | 2-NO2-4-OC5H11 | |
| I-107 | — | H | H | 2-NO2-4-OCH2OCH3 | |
| I-108 | — | H | H | 2-NO2-4-OCH2OCH3 | |
| I-109 | — | H | H | 2-NO2-4-OCH3 | mp 76–81(dec) |
| I-110 | 5-CH3 | H | H | 2-NO2-4-OCH3 | |
| I-111 | 1-CH3 | H | H | 2-NO2-4-OCH3 | |
| I-112 | 5,5-(CH3)2 | H | H | 2-NO2-4-OCH3 | |
| I-113 | 1,5,5-(CH3)3 | H | H | 2-NO2-4-OCH3 | |
| I-114 | —(n = 0) | CH3 | CH3 | 2-NO2-4-OCH3 | |

TABLE 1-continued

Structural Formula

[Structure: cyclohexanedione with cyclopropane fused ring bearing R3, R4; (R2)n substituents; benzoyl group with Xm on phenyl]

| No. | (R2)n | R3 | R4 | Xm | Physical Properties |
|---|---|---|---|---|---|
| I-115 | — | H | H | 2-NO2-4-ORx | |
| I-116 | — | H | H | 2-NO2-4-ORy | |
| I-117 | — | H | H | 2-NO2-4-ORz | |
| I-118 | — | H | H | 2-NO2-4-SCH(CH3)COOC2H5 | |
| I-119 | — | H | H | 2-NO2-4-SCH2CH2OCH2CH2OCH3 | |
| I-120 | — | H | H | 2-NO2-4-SCH2CH2OCH3 | |
| I-121 | —(n = 0) | H | H | 2-NO2-4-SCH2Cl | |
| I-122 | — | H | H | 2-NO2-4-SCH2CCN | |
| I-123 | — | H | H | 2-NO2-4-SCH2COCH3 | |
| I-124 | — | H | H | 2-NO2-4-SCH2C≡CH | |
| I-125 | — | H | H | 2-NO2-4-SCH2OCH3 | |
| I-126 | 5-CH3 | H | H | 2-NO2-4-SCH2OCH3 | powder(trans) |
| I-127 | 1-CH3 | H | H | 2-NO2-4-SCH2OCH3 | |
| I-128 | 5,5-(CH3)2 | H | H | 2-NO2-4-SCH2OCH3 | |
| I-129 | 1,5,5-(CH3)3 | H | H | 2-NO2-4-SCH2OCH3 | |
| I-130 | —(n = 0) | CH3 | CH3 | 2-NO2-4-SCH2OCH3 | |
| I-131 | — | H | H | 2-NO2-4-SCH2Rz | |
| I-132 | — | H | H | 2-NO2-4-SCH2SCH3 | |
| I-133 | — | H | H | 2-NO2-4-SCH3 | mp 98–100 |
| I-134 | — | H | H | 2-NO2-4-SO2CH(CH3)COOC2H5 | |
| I-135 | — | H | H | 2-NO2-4-SO2CH2Cl | |
| I-136 | 5-CH3 | H | H | 2-NO2-4-SO2CH2Cl | |
| I-137 | 1-CH3 | H | H | 2-NO2-4-SO2CH2Cl | |
| I-138 | 5,5-(CH3)2 | H | H | 2-NO2-4-SO2CH2Cl | |
| I-139 | 1,5,5-(CH3)3 | H | H | 2-NO2-4-SO2CH2Cl | |
| I-140 | —(n = 0) | CH3 | CH3 | 2-NO2-4-SO2CH2Cl | |
| I-141 | — | H | H | 2-NO2-4-SO2CH2COOCH3 | |
| I-142 | — | H | H | 2-NO2-4-SO2CH2OCH3 | |
| I-143 | — | H | H | 2-NO2-4-SO2CH3 | mp 161-2 |
| I-144 | 5-CH3 | H | H | 2-NO2-4-SO2CH3 | mp 164–5(dec)(trans) |
| I-145 | 1-CH3 | H | H | 2-NO2-4-SO2CH3 | powder |
| I-146 | 5,5-(CH3)2 | H | H | 2-NO2-4-SO2CH3 | mp 159–161 |
| I-147 | 1,5,5-(CH3)3 | H | H | 2-NO2-4-SO2CH3 | |
| I-148 | —(n = 0) | CH3 | CH3 | 2-NO2-4-SO2CH3 | |
| I-149 | — | H | H | 2-NO2-4-SO2CH3-5-Cl | |
| I-150 | — | H | H | 2-NO2-4-SO2CHCl2 | |
| I-151 | —(n = 0) | H | H | 2-NO2-4-SPh | |
| I-152 | — | H | H | 2-NO2-4-SRz | |
| I-153 | — | H | H | 2-NO2-5-CH3 | |
| I-154 | — | H | H | 2-OCH3 | |
| I-155 | — | H | H | 2-OCH3-3-OCH3-4-OCH3 | |
| I-156 | — | H | H | 2-Ph | |
| I-157 | — | H | H | 2-SCF3 | |
| I-158 | — | H | H | 2-SCH3 | |
| I-159 | — | H | H | 2-SO2CF3 | |
| I-160 | — | H | H | 2-SO2CCH3 | |
| I-161 | — | H | H | 2-SO2CCH3-4-NO2 | |
| I-162 | — | H | H | 2-SOCF3 | |
| I-163 | 5-CH3 | H | H | 2-Cl-4-Cl | mp 86.5–9.5(trans) |
| I-164 | 1-CH3 | H | H | 2-Cl-4-Cl | mp 92–4 |
| I-165 | 6-CH3 | H | H | 2-NO2-4-Cl | nD 25.5 1.6050 |
| I-166 | —(n = 0) | CH3 | H | 2-NO2-4-Cl | mp 107-9 |
| I-167 | — | H | H | 2-CH3-4-CH3 | mp 83–6 |
| I-168 | 5-CH3 | H | H | 2-Cl-3-OCH3-4-SO2C2H5 | mp 120–2(trans) |
| I-169 | 5,6-(CH3)2 | H | H | 2-NO2-4-Cl | powder |
| I-170 | 5-CH3 | H | H | 2-Cl-3-CH3-4-SO2CH3 | mp 157-9(trans) |
| I-171 | 5-CH3-5-COOC2H5 | H | H | 2-NO2 | mp 133.5–4.5(trans) |
| I-172 | 5-CH3 | H | H | 2-Cl-4-SO2CH3 | mp 129-14 131(trans) |
| I-173 | 5-CH3 | H | H | 2-Cl-4-SO2CH3-5-Cl | mp 141–4(trans) |
| I-174 | 5,6-(CH3)2 | H | H | 2-NO2-4-SO2CH3 | powder |
| I-175 | 6-CH3 | H | H | 2-NO2-4-SO2CH3 | oil |
| I-176 | 5,6-(CH3)2 | H | H | 2-Cl-3-OCH3-4-SO2CH3 | powder |
| I-177 | 5-CH3 | H | H | 2-CH3-3-Br-4-SO2CH3 | mp 183–5(trans) |
| I-178 | 1-CH3 | H | H | 2-CH3-3-Br-4-SO2CH3 | powder |
| I-179 | 5-CH3 | H | H | 2-Cl-3-CH2OCH3-4-SO2CH3 | powder (trans) |
| I-180 | 1-CH3 | H | H | 2-Cl-3-CH2OCH3-4-SO2CH3 | powder |
| I-181 | 1,5-(CH3)2 | H | H | 2-NO2-4-Cl | mp 122–3 |
| I-182 | 5-CH3 | H | H | 2-Cl-4-SO2CH3-5-OCH3 | powder(trans) |
| I-183 | 5-CH3 | H | H | 2-Cl-3-OCH2CH=CH2-4-SO2CH3 | powder(trans) |
| I-184 | 5-CH3 | H | H | 2-Cl-3-CO2CH3-4-SO2CH3 | |
| I-185 | 5-CH3 | H | H | 2-Cl-4-CF3 | nD 25.5 1.5369(trans) |
| I-186 | 5-CH3 | H | H | 2-Cl-3-OCH2(Br)C=CH2-4-SO2CH3 | powder(trans) |

TABLE 1-continued

Structural Formula

| No. | (R2)n | R3 | R4 | Xm | Physical Properties |
|---|---|---|---|---|---|
| I-187 | 5-CH3 | H | H | 2-Cl-3-OCH2C≡CH-4-SO2CH3 | mp 184–7(trans) |
| I-188 | 5-CH3 | H | H | 2-Cl-3-OCH2Cl-4-SO2CH3 | mp 103–5(trans) |
| I-189 | 5-CH3-5-CO2C2H5 | H | H | 2-CH3-3-CH3-4-SO2CH3 | oil(trans) |
| I-190 | 5-CH3 | H | H | 2-Cl-3-OC2H5-4-SO2CH3 | powder(trans) |
| I-191 | 5-CH(CH3)2 | H | H | 2-NO2-4-Cl | mp 161–2(trans) |
| I-192 | 5-CH3 | H | H | 2-CH3-3-CH3-4-SO2CH3 | mp 164–7(cis) |
| I-193 | 5-CH3 | H | H | 2-Cl-4-OCF3 | nD 25.5 1.5248(trans) |
| I-194 | 5-CH3 | H | H | 2-CH(CH3)2O4OCl | nD 25.0 1.5710(trans) |
| I-195 | 5-CH3 | H | H | 2-Cl-3-OCH3-4-SO2CH3 | mp 132–5(cis) |
| I-196 | 5-CH3 | H | H | 2-CH2OCH3-4-SO2CH3 | nD 24.5 1.5662(trans) |
| I-197 | 5-C2H5 | H | H | 2-NO2-4-Cl | mp 109–111(trans) |
| I-198 | 5-CH(CH3)2 | H | H | 2-NO2-4-SO2CH3 | mp 88–90(trans) |
| I-199 | 5-CH3-5-CO2C2H5 | H | H | 2-NO2-4-SO2CH3 | |
| I-200 | 5-CH3 | H | H | 2-Cl-3-CH3-4-SO2CH3 | powder(cis) |
| I-201 | 5-CH3 | H | H | 2-NO2-4-SO2CF2H | mp 176–8(dec)(trans) |
| I-202 | 5-CH3-5-CO2C2H5 | H | H | 2-Cl-3-OCH3-4-SO2CH3 | nD 24.5 1.5649(trans) |
| I-203 | 5-OCH3 | H | H | 2-NO2-4-SO2CH3 | powder(trans) |
| I-204 | 5-CH3 | H | H | 2-Cl-4-SO2CH3 | powder(cis) |
| I-205 | 5-CH3 | H | H | 2-CH3-3-Cl-4-SO2CH3 | mp 165–7(trans) |
| I-206 | 5-CH3 | H | H | 2-NO2-4-COCH3 | mp 146–8(trans) |
| I-207 | 5-CH3 | H | H | 2-Cl-4-OCHF2 | nD 24 1.5592(trans) |
| I-208 | 5-CH3 | H | H | 2-CH3-3-Br-4-SO2CH3 | mp 172–4(cis) |
| I-209 | 5-CH3 | H | H | 2-Cl-3-Cl-4-SO2CH3 | powder(cis) |
| I-210 | 5,5-(CH3)2-6-CH3 | H | H | 2-NO2-4-SO2CH3 | mp 175–7 |
| I-211 | 1-CH3 | H | H | 2-NO2-3-OCH3-4-Cl | powder |
| I-212 | 5-CH3 | H | H | 2-NO2-3-OCH3-4-Cl | powder(trans) |
| I-213 | 1-SCH3 | H | H | 2-NO2-4-Cl | mp 168–170 |
| I-214 | 5-CH3 | H | H | 2-CL-3-Cl-4-SO2CH3 | Na salt 180(dec)(trans) |
| I-215 | 5-CH3 | H | H | 2-Cl-4-OCF2CHF2 | nD 25.5 1.5276(trans) |
| I-216 | 5-CH3 | H | H | 2-NO2-4-CHF2 | mp 163–5(trans) |
| I-217 | 5-CH3 | H | H | 2-NO2-4-SO2CH3 | powder(cis) |
| I-218 | 5-CH3 | H | H | 2-CH3-3-NO2-4-SO2CH3 | mp 197–9(trans) |
| I-219 | 5-CH3-5-SO2CH3 | H | H | 2-NO2-4-Cl | mp 184–6 |
| I-220 | 5-CH3-5-SCH3 | H | H | 2-NO2-4-Cl | mp 144–5 |
| I-221 | 5-CH3 | H | H | 2-NO2-4-CF3 | mp 90–2(cis) |
| I-222 | 5-CH3 | H | H | 2-NO2--3-CH3-4-SO2CH3 | mp 139–141(trans) |
| I-223 | 5-CH3-5-CO2C2H5 | H | H | 2-NO2-4-CF3 | oil |
| I-224 | 5-CH3 | H | H | 2-NO2-4-Cl | mp 104–8(cis) |
| I-225 | 5-CH3 | H | H | 2-OCH3-3-OCH3-4-OCH3 | powder(trans) |
| I-226 | 5-CH3 | H | H | 2-Cl-3-Cl-4-Cl | mp 111–2(trans) |
| I-227 | 5-CH3 | H | H | 2-Cl-3-Cl-4-OCH3 | mp 113–4(trans) |
| I-228 | 5-Br | H | H | 2-NO2-4-Cl | mp 158–160(trans) |
| I-229 | 5-CH2CH2OCH3 | H | H | 2-NO2-4-Cl | nD 23 1.5850(trans) |
| I-230 | 5-SCH2CH3 | H | H | 2-NO2-4-Cl | mp 119–120(trans) |
| I-231 | 5-CH3 | H | H | 2-NO2-4-SO2N(CH3)2 | mp 142–5(dec)(trans) |
| I-232 | 5-CH3 | H | H | 2-CH3-3-CH3-4-SO2CH3 | H2NCH3 salt mp 139–140(dec)(trans) |
| I-233 | 5-CH3 | H | H | 2-CH3-3-CH3-4-SO2CH3 | Na salt mp 168(dec)(trans) |
| I-234 | 5-CH3 | H | H | 2-Cl-3-OCH3-4-SO2CH3 | Na salt mp 158(dec)(cis) |
| I-235 | 5-CH3 | H | H | 2-CH3-3-CH3-4-Cl | mp 117–8(trans) |
| I-236 | 5-CH3 | H | H | 2-NO2-4-NO2 | mp 151–2(trans) |
| I-237 | 5-CH3 | H | H | 2-NO2-4-SCH3 | mp 129–132(trans) |
| I-238 | 1-CH3 | H | H | 2-NO2-4-SHC3 | mp 70–4 |
| I-239 | 5,5-(Br)2 | H | H | 2-CH3-3-CH3-4-SO2CH3 | mp 129–131 |
| I-240 | 5-SCH3 | H | H | 2-CH3-3-CH3-4-SO2CH3 | mp 140–2(trans) |
| I-241 | 5-CH2CH2OCH3 | H | H | 2-NO2-4-SO2CH3 | powder(trans) |
| I-242 | 5-CH3 | H | H | 2-NO2-4-ORx | powder(trans) |
| I-243 | 5-CH3 | H | H | 2-CH3-3-Cl-4-OCH3 | mp 115–7(trans) |
| I-244 | 5-CH3 | H | H | 2-OCH3-4-SO2CH3 | powder(trans) |
| I-245 | 5-CH3 | H | H | 2-CF3-4-SO2CH3 | powder(trans) |
| I-246 | 5-CH3 | H | H | 2-NO2-4-SCH2SCH3 | powder(trans) |
| I-247 | 5-CH3 | H | H | 2-NO2-4-SO2CH2OCH3 | mp 147–150(trans) |
| I-248 | 5-SO2CH2CH3 | H | H | 2-NO2-4-Cl | mp 163–5(trans) |
| I-249 | 5-CH3 | H | H | 2-CF3-4-Cl | powder(trans) |
| I-250 | 1-CH3 | H | H | 2-CF3-4-Cl | powder |
| I-251 | 1-CH2CH2OCH3 | H | H | 2-NO2-4-Cl | nD 23 1.5842 |
| I-252 | 1-CH3 | H | H | 2-NO2-4-NO2 | powder |
| I-253 | 1-CH3 | H | H | 2-NO2-4-Orx | powder |
| I-254 | 1-CH3 | H | H | 2-CF3-4-SO2CH3 | powder |
| I-255 | 1-CH3 | H | H | 2-NO2-4-SCH2OCH3 | powder |
| I-256 | 5-CH3 | H | H | 2-Cl-3-Cl-4-OCH2OCH3 | powder(trans) |
| I-257 | —(N = 0) | H | H | 2-NO2-4-SCH2OCH3 | powder |
| I-258 | 5-CH3 | H | H | 2-OC2H5-3-Cl-4-SO2CH3 | mp 152–6(cis) |

TABLE 1-continued

Structural Formula

| No. | (R2)n | R3 | R4 | Xm | Physical Properties |
|---|---|---|---|---|---|
| I-259 | —(N = 0) | H | H | 2-NO2-4-NHCOCH3 | powder |
| I-260 | — | H | H | 2-NO2-4-SCH2CH=CH2 | oil |
| I-261 | 5-CH3 | H | H | 2-F-3-F-4-F-5-F | mp 172–4(trans) |
| I-262 | 5-CH3 | H | H | 2-CH3-3-CH3-4-SO2CH3 | Na salt mp 230(dec)(cis) |
| I-263 | 5-CH3 | H | H | 2-Cl-3-CH3-4-SO2CH3 | Na salt mp 180–2(dec)(cis) |
| I-264 | 5-CH3 | H | H | 2-CH3-3-Br-4-SO2CH3 | Na salt mp 223(dec)(cis) |
| I-265 | 5-CH3 | H | H | 2-Cl-3-Cl-4-OCH2SCH3 | powder(trans) |
| I-266 | 5-CH3 | H | H | 2-Cl-3-Cl-4-OCH2Ph | mp 148–9(trans) |
| I-267 | 5-CH3 | H | H | 2-Cl-3-Cl-4-OH | mp 169–171(dec)(trans) |
| I-268 | 5-CH3 | H | H | 2-CH3-3-CH3-4-SO2CH3 | K salt mp 198–200(dec)(trans) |
| I-269 | 5-CH3 | H | H | 2-CH3-3-CH3-4-SO2CH3 | Li salt mp > 260(trans) |
| I-270 | 5-CH3 | H | H | 2-CH3-3-CH3-4-SO2CH3 | ½ Ca salt mp > 260(trans) |
| I-271 | 5-CH3 | H | H | 2-CH3-3-CH3-4-SO2CH3 | ½ Cu salt mp > 260(trans) |
| I-272 | 5-CH3 | H | H | 2-Cl-3-OCH3-4-SO2CH3 | K salt mp 188–190(dec)(cis) |
| I-273 | 5-CH3 | H | H | 2-Cl-3-OCH3-4-SO2CH3 | Li salt mp 178–180(dec)(cis) |
| I-274 | 5-CH3 | H | H | 2-Cl-3-OCH3-4-SO2CH3 | ½ Ca salt mp > 225(dec)(cis) |
| I-275 | 5-CH3 | H | H | 2-Cl-3-OCH3-4-SO2CH3 | ½ Cu salt mp 210–212(cis) |

TABLE 2

Structural

| No. | (R2)n | R3 | R4 | Hetero ring | Xm | Physical Properties |
|---|---|---|---|---|---|---|
| II-1 | 5-CH3 | H | H | 2-pyridine | 5-CF3 | |
| II-2 | 5-CH3 | H | H | 2-pyridine | 5-CH2OCH3 | |
| II-3 | 5-CH3 | H | H | 2-pyridine | 5-CH2SCH3 | |
| II-4 | 5-CH3 | H | H | 2-pyridine | 5-SCH3 | |
| II-5 | 5-CH3 | H | H | 2-pyridine | 5-SOCH3 | |
| II-6 | 5-CH3 | H | H | 2-pyridine | 5-SO2CH3 | |
| II-7 | 5-CH3 | H | H | 2-pyridine | 5-SC2H5 | |
| II-8 | 5-CH3 | H | H | 2-pyridine | 5-SOC2H5 | |
| II-9 | 5-CH3 | H | H | 2-pyridine | 5-SO2C2H5 | |
| II-10 | 5-CH3 | H | H | 2-pyridine | 5-CH3 | |
| II-11 | 5-CH3 | H | H | 2-pyridine | 5-NO2 | |
| II-12 | 5-CH3 | H | H | 2-pyridine | 5-CN | |
| II-13 | 6-CH3 | H | H | 2-pyridine | 5-CF3 | |
| II-14 | 6-CH3 | H | H | 2-pyridine | 5-CH2OCH3 | |
| II-15 | 6-CH3 | H | H | 2-pyridine | 5-CH2SCH3 | |
| II-16 | 6-CH3 | H | H | 2-pyridine | 5-SCH3 | |
| II-17 | 6-CH3 | H | H | 2-pyridine | 5-SOCH3 | |
| II-18 | 6-CH3 | H | H | 2-pyridine | 5-SO2CH3 | |
| II-19 | 6-CH3 | H | H | 2-pyridine | 5-SC2H5 | |
| II-20 | 6-CH3 | H | H | 2-pyridine | 5-SOC2H5 | |
| II-21 | 6-CH3 | H | H | 2-pyridine | 5-SO2C2H5 | |
| II-22 | 6-CH3 | H | H | 2-pyridine | 5-CH3 | |

TABLE 2-continued

Structural

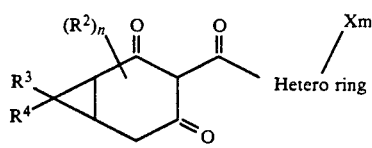

| No. | (R2)n | R3 | R4 | Hetero ring | Xm | Physical Properties |
|---|---|---|---|---|---|---|
| II-23 | 6-CH3 | H | H | 2-pyridine | 5-NO2 | |
| II-24 | 6-CH3 | H | H | 2-pyridine | 5-CN | |
| II-25 | —(n = 0) | H | H | 2-pyridine | 5-CF3 | |
| II-26 | — | H | H | 2-pyridine | 5-CH2OCH3 | |
| II-27 | — | H | H | 2-pyridine | 5-CH2SCH3 | |
| II-28 | — | H | H | 2-pyridine | 5-SCH3 | |
| II-29 | — | H | H | 2-pyridine | 5-SOCH3 | |
| II-30 | — | H | H | 2-pyridine | 5-SO2CH3 | |
| II-31 | —(n = 0) | H | H | 2-pyridine | 5-SC2H5 | |
| II-32 | — | H | H | 2-pyridine | 5-SOC2H5 | |
| II-33 | — | H | H | 2-pyridine | 5-SO2C2H5 | |
| II-34 | — | H | H | 2-pyridine | 5-CH3 | |
| II-35 | — | H | H | 2-pyridine | 5-NO2 | |
| II-36 | — | H | H | 2-pyridine | 5-CN | |
| II-37 | 1-CH3 | H | H | 2-pyridine | 5-CF3 | |
| II-38 | 1-CH3 | H | H | 2-pyridine | 5-CH2OCH3 | |
| II-39 | 1-CH3 | H | H | 2-pyridine | 5-CH2SCH3 | |
| II-40 | 1-CH3 | H | H | 2-pyridine | 5-SCH3 | |
| II-41 | 1-CH3 | H | H | 2-pyridine | 5-SOCH3 | |
| II-42 | 1-CH3 | H | H | 2-pyridine | 5-SO2CH3 | |
| II-43 | 1-CH3 | H | H | 2-pyridine | 5-SC2H5 | |
| II-44 | 1-CH3 | H | H | 2-pyridine | 5-SOC2H5 | |
| II-45 | 1-CH3 | H | H | 2-pyridine | 5-SO2C2H5 | |
| II-46 | 1-CH3 | H | H | 2-pyridine | 5-CH3 | |
| II-47 | 1-CH3 | H | H | 2-pyridine | 5-NO2 | |
| II-48 | 1-CH3 | H | H | 2-pyridine | 5-CN | |
| II-49 | 5-CH3 | CH3 | CH3 | 2-pyridine | 5-CF3 | |
| II-50 | 5-CH3 | CH3 | CH3 | 2-pyridine | 5-CH2OCH3 | |
| II-51 | 5-CH3 | CH3 | CH3 | 2-pyridine | 5-CH2SCH3 | |
| II-52 | 5-CH3 | CH3 | CH3 | 2-pyridine | 5-SCH3 | |
| II-53 | 5-CH3 | CH3 | CH3 | 2-pyridine | 5-SOCH3 | |
| II-54 | 5-CH3 | CH3 | CH3 | 2-pyridine | 5-SO2CH3 | |
| II-55 | 5-CH3 | CH3 | CH3 | 2-pyridine | 5-SC2H5 | |
| II-56 | 5-CH3 | CH3 | CH3 | 2-pyridine | 5-SOC2H5 | |
| II-57 | 5-CH3 | CH3 | CH3 | 2-pyridine | 5-SO2C2H5 | |
| II-58 | 5-CH3 | CH3 | CH3 | 2-pyridine | 5-CH3 | |
| II-59 | 5-CH3 | CH3 | CH3 | 2-pyridine | 5-NO2 | |
| II-60 | 5-CH3 | CH3 | CH3 | 2-pyridine | 5-CN | |
| II-61 | —(n = 0) | CH3 | CH3 | 2-pyridine | 5-CF3 | |
| II-62 | — | CH3 | CH3 | 2-pyridine | 5-CH2OCH3 | |
| II-63 | — | CH3 | CH3 | 2-pyridine | 5-CH2SCH3 | |
| II-64 | — | CH3 | CH3 | 2-pyridine | 5-SCH3 | |
| II-65 | — | CH3 | CH3 | 2-pyridine | 5-SOCH3 | |
| II-66 | — | CH3 | CH3 | 2-pyridine | 5-SO2CH3 | |
| II-67 | — | CH3 | CH3 | 2-pyridine | 5-SC2H5 | |
| II-68 | — | CH3 | CH3 | 2-pyridine | 5-SOC2H5 | |
| II-69 | — | CH3 | CH3 | 2-pyridine | 5-SO2C2H5 | |
| II-70 | — | CH3 | CH3 | 2-pyridine | 5-CH3 | |
| II-71 | — | CH3 | CH3 | 2-pyridine | 5-NO2 | |
| II-72 | — | CH3 | CH3 | 2-pyridine | 5-CN | |
| II-73 | 1-CH3 | CH3 | CH3 | 2-pyridine | 5-CF3 | |
| II-74 | 1-CH3 | CH3 | CH3 | 2-pyridine | 5-CH2OCH3 | |
| II-75 | 1-CH3 | CH3 | CH3 | 2-pyridine | 5-CH2SCH3 | |
| II-76 | 1-CH3 | CH3 | CH3 | 2-pyridine | 5-SCH3 | |
| II-77 | 1-CH3 | CH3 | CH3 | 2-pyridine | 5-SOCH3 | |
| II-78 | 1-CH3 | CH3 | CH3 | 2-pyridine | 5-SO2CH3 | |
| II-79 | 1-CH3 | CH3 | CH3 | 2-pyridine | 5-SC2H5 | |
| II-80 | 1-CH3 | CH3 | CH3 | 2-pyridine | 5-SOC2H5 | |
| II-81 | 1-CH3 | CH3 | CH3 | 2-pyridine | 5-SO2C2H5 | |
| II-82 | 1-CH3 | CH3 | CH3 | 2-pyridine | 5-CH3 | |
| II-83 | 1-CH3 | CH3 | CH3 | 2-pyridine | 5-NO2 | |
| II-84 | 1-CH3 | CH3 | CH3 | 2-pyridine | 5-CN | |
| II-85 | 5-CH3 | H | H | 3-pyridine | 2-CF3 | |
| II-86 | 5-CH3 | H | H | 3-pyridine | 2-CF3-6-Cl | |
| II-87 | 5-CH3 | H | H | 3-pyridine | 2-CH2OCH3 | |
| II-88 | 5-CH3 | H | H | 3-pyridine | 2-CH2OCH3-6-CH3 | |
| II-89 | 5-CH3 | H | H | 3-pyridine | 2-CH2OCH3-6-Cl | |
| II-90 | 5-CH3 | H | H | 3-pyridine | 2-CH2OCH3-6-SCH3 | |
| II-91 | 5-CH3 | H | H | 3-pyridine | 2-CH2SCH3 | |
| II-92 | 5-CH3 | H | H | 3-pyridine | 2-CH2SCH3-6-CH3 | |
| II-93 | 5-CH3 | H | H | 3-pyridine | 2-CH2SCH3-6-Cl | |

TABLE 2-continued

Structural

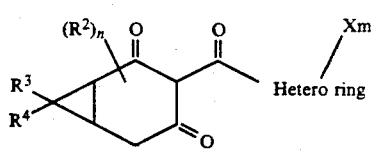

| No. | (R2)n | R3 | R4 | Hetero ring | Xm | Physical Properties |
|---|---|---|---|---|---|---|
| II-94 | 5-CH3 | H | H | 3-pyridine | 2-CH2SO2CH3 | |
| II-95 | 5-CH3 | H | H | 3-pyridine | 2-CH2SO2CH3-6-CH3 | |
| II-96 | 5-CH3 | H | H | 3-pyridine | 2-CH2SO2CH3-6-Cl | |
| II-97 | 5-CH3 | H | H | 3-pyridine | 2-CH2SO2CH3-6-Cl | |
| II-98 | 5-CH3 | H | H | 3-pyridine | 2-CH3 | |
| II-99 | 5-CH3 | H | H | 3-pyridine | 2-CH3-6-CH2SCH3 | |
| II-100 | 5-CH3 | H | H | 3-pyridine | 2-CH3-6-CH2SCH3 | |
| II-101 | 5-CH3 | H | H | 3-pyridine | 2-CH3-6-CH3 | |
| II-102 | 5-CH3 | H | H | 3-pyridine | 2-CH3-6-Cl | mp 140–1(trans) |
| II-103 | 5-CH3 | H | H | 3-pyridine | 2-CH3-6-CN | |
| II-104 | 5-CH3 | H | H | 3-pyridine | 2-CH3-6-OCH3 | |
| II-105 | 5-CH3 | H | H | 3-pyridine | 2-CH3-6-SCH2Cl | |
| II-106 | 5-CH3 | H | H | 3-pyridine | 2-CH3-6-SCH2OCH3 | |
| II-107 | 5-CH3 | H | H | 3-pyridine | 2-CH3-6-SCH3 | |
| II-108 | 5-CH3 | H | H | 3-pyridine | 2-CH3-6-SO2CH2Cl | |
| II-109 | 5-CH3 | H | H | 3-pyridine | 2-CH3-6-SO2CH3 | mp 162–4(trans) |
| II-110 | 5-CH3 | H | H | 3-pyridine | 2-CN | |
| II-111 | 5-CH3 | H | H | 3-pyridine | 2-CN-6-CH3 | |
| II-112 | 5-CH3 | H | H | 3-pyridine | 2-CN-6-Cl | |
| II-113 | —(n = 0) | H | H | 3-pyridine | 2-CF3 | |
| II-114 | — | H | H | 3-pyridine | 2-CF3-6-Cl | |
| II-115 | — | H | H | 3-pyridine | 2-CH2OCH3 | |
| II-116 | — | H | H | 3-pyridine | 2-CH2OCH3-6-CH3 | |
| II-117 | — | H | H | 3-pyridine | 2-CH2OCH3-6-Cl | |
| II-118 | — | H | H | 3-pyridine | 2-CH2OCH3-6-SCH3 | |
| II-119 | — | H | H | 3-pyridine | 2-CH2SCH3 | |
| II-120 | — | H | H | 3-pyridine | 2-CH2SCH3-6-CH3 | |
| II-121 | —(n = 0) | H | H | 3-pyridine | 2-CH2SCH3-6-Cl | |
| II-122 | — | H | H | 3-pyridine | 2-CH2SO2CH3 | |
| II-123 | — | H | H | 3-pyridine | 2-CH2SO2CH3-6-CH3 | |
| II-124 | — | H | H | 3-pyridine | 2-CH2SO2CH3-6-Cl | |
| II-125 | — | H | H | 3-pyridine | 2-CH2SO2CH3-6-Cl | |
| II-126 | — | H | H | 3-pyridine | 2-CH3 | |
| II-127 | — | H | H | 3-pyridine | 2-CH3-6-CH2SCH3 | |
| II-128 | — | H | H | 3-pyridine | 2-CH3-6-CH2SCH3 | |
| II-129 | — | H | H | 3-pyridine | 2-CH3-6-CH3 | |
| II-130 | — | H | H | 3-pyridine | 2-CH3-6-Cl | mp 109–111 |
| II-131 | — | H | H | 3-pyridine | 2-CH3-6-CN | |
| II-132 | — | H | H | 3-pyridine | 2-CH3-6-OCH3 | |
| II-133 | — | H | H | 3-pyridine | 2-CH3-6-SCH2Cl | |
| II-134 | — | H | H | 3-pyridine | 2-CH3-6-SCH2OCH3 | |
| II-135 | — | H | H | 3-pyridine | 2-CH3-6-SCH3 | |
| II-136 | — | H | H | 3-pyridine | 2-CH3-6-SO2CH2Cl | |
| II-137 | — | H | H | 3-pyridine | 2-CH3-6-SO2CH3 | mp 163–5 |
| II-138 | — | H | H | 3-pyridine | 2-CN | |
| II-139 | — | H | H | 3-pyridine | 2-CN-6-CH3 | |
| II-140 | — | H | H | 3-pyridine | 2-CN-6-Cl | |
| II-141 | 1-CH3 | H | H | 3-pyridine | 2-CF3 | |
| II-142 | 1-CH3 | H | H | 3-pyridine | 2-CF3-6-Cl | |
| II-143 | 1-CH3 | H | H | 3-pyridine | 2-CH2OCH3 | |
| II-144 | 1-CH3 | H | H | 3-pyridine | 2-CH2OCH3-6-CH3 | |
| II-145 | 1-CH3 | H | H | 3-pyridine | 2-CH2OCH3-6-Cl | |
| II-146 | 1-CH3 | H | H | 3-pyridine | 2-CH2OCH3-6-SCH3 | |
| II-147 | 1-CH3 | H | H | 3-pyridine | 2-CH2SCH3 | |
| II-148 | 1-CH3 | H | H | 3-pyridine | 2-CH2SCH3-6-CH3 | |
| II-149 | 1-CH3 | H | H | 3-pyridine | 2-CH2SCH3-6-Cl | |
| II-150 | 1-CH3 | H | H | 3-pyridine | 2-CH2SO2CH3 | |
| II-151 | 1-CH3 | H | H | 3-pyridine | 2-CH2SO2CH3-6-CH3 | |
| II-152 | 1-CH3 | H | H | 3-pyridine | 2-CH2SO2CH3-6-Cl | |
| II-153 | 1-CH3 | H | H | 3-pyridine | 2-CH2SO2CH3-6-Cl | |
| II-154 | 1-CH3 | H | H | 3-pyridine | 2-CH3 | |
| II-155 | 1-CH3 | H | H | 3-pyridine | 2-CH3-6-CH2SCH3 | |
| II-156 | 1-CH3 | H | H | 3-pyridine | 2-CH3-6-CH2SCH3 | |
| II-157 | 1-CH3 | H | H | 3-pyridine | 2-CH3-6-CH3 | |
| II-158 | 1-CH3 | H | H | 3-pyridine | 2-CH3-6-Cl | |
| II-159 | 1-CH3 | H | H | 3-pyridine | 2-CH3-6-CN | |
| II-160 | 1-CH3 | H | H | 3-pyridine | 2-CH3-6-OCH3 | |
| II-161 | 1-CH3 | H | H | 3-pyridine | 2-CH3-6-SCH2Cl | |
| II-162 | 1-CH3 | H | H | 3-pyridine | 2-CH3-6-SCH2OCH3 | |
| II-163 | 1-CH3 | H | H | 3-pyridine | 2-CH3-6-SCH3 | |
| II-164 | 1-CH3 | H | H | 3-pyridine | 2-CH3-6-SO2CH2Cl | |

TABLE 2-continued

Structural

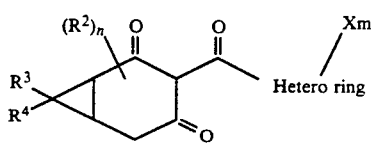

| No. | (R2)n | R3 | R4 | Hetero ring | Xm | Physical Properties |
|---|---|---|---|---|---|---|
| II-165 | 1-CH3 | H | H | 3-pyridine | 2-CH3-6-SO2CH3 | oil |
| II-166 | 1-CH3 | H | H | 3-pyridine | 2-CN | |
| II-167 | 1-CH3 | H | H | 3-pyridine | 2-CN-6-CH3 | |
| II-168 | 1-CH3 | H | H | 3-pyridine | 2-CN-6-Cl | |
| II-169 | 5-CH3 | CH3 | CH3 | 3-pyridine | 2-CF3 | |
| II-170 | 5-CH3 | CH3 | CH3 | 3-pyridine | 2-CF3-6-Cl | |
| II-171 | 5-CH3 | CH3 | CH3 | 3-pyridine | 2-CH2OCH3 | |
| II-172 | 5-CH3 | CH3 | CH3 | 3-pyridine | 2-CH2OCH3-6-CH3 | |
| II-173 | 5-CH3 | CH3 | CH3 | 3-pyridine | 2-CH2OCH3-6-Cl | |
| II-174 | 5-CH3 | CH3 | CH3 | 3-pyridine | 2-CH2OCH3-6-SCH3 | |
| II-175 | 5-CH3 | CH3 | CH3 | 3-pyridine | 2-CH2SCH3 | |
| II-176 | 5-CH3 | CH3 | CH3 | 3-pyridine | 2-CH2SCH3-6-CH3 | |
| II-177 | 5-CH3 | CH3 | CH3 | 3-pyridine | 2-CH2SCH3-6-Cl | |
| II-178 | 5-CH3 | CH3 | CH3 | 3-pyridine | 2-CH2SO2CH3 | |
| II-179 | 5-CH3 | CH3 | CH3 | 3-pyridine | 2-CH2SO2CH3-6-CH3 | |
| II-180 | 5-CH3 | CH3 | CH3 | 3-pyridine | 2-CH2SO2CH3-6-Cl | |
| II-181 | 5-CH3 | CH3 | CH3 | 3-pyridine | 2-CH2SO2CH3-6-Cl | |
| II-182 | 5-CH3 | CH3 | CH3 | 3-pyridine | 2-CH3 | |
| II-183 | 5-CH3 | CH3 | CH3 | 3-pyridine | 2-CH3-6-CH2SCH3 | |
| II-184 | 5-CH3 | CH3 | CH3 | 3-pyridine | 2-CH3-6-CH2SCH3 | |
| II-185 | 5-CH3 | CH3 | CH3 | 3-pyridine | 2-CH3-6-CH3 | |
| II-186 | 5-CH3 | CH3 | CH3 | 3-pyridine | 2-CH3-6-Cl | |
| II-187 | 5-CH3 | CH3 | CH3 | 3-pyridine | 2-CH3-6-CN | |
| II-188 | 5-CH3 | CH3 | CH3 | 3-pyridine | 2-CH3-6-OCH3 | |
| II-189 | 5-CH3 | CH3 | CH3 | 3-pyridine | 2-CH3-6-SCH2Cl | |
| II-190 | 5-CH3 | CH3 | CH3 | 3-pyridine | 2-CH3-6-SCH2OCH3 | |
| II-191 | 5-CH3 | CH3 | CH3 | 3-pyridine | 2-CH3-6-SCH3 | |
| II-192 | 5-CH3 | CH3 | CH3 | 3-pyridine | 2-CH3-6-SO2CH2Cl | |
| II-193 | 5-CH3 | CH3 | CH3 | 3-pyridine | 2-CH3-6-SO2CH3 | |
| II-194 | 5-CH3 | CH3 | CH3 | 3-pyridine | 2-CN | |
| II-195 | 5-CH3 | CH3 | CH3 | 3-pyridine | 2-CN-6-CH3 | |
| II-196 | 5-CH3 | CH3 | CH3 | 3-pyridine | 2-CN-6-Cl | |
| II-197 | —(n = 0) | CH3 | CH3 | 3-pyridine | 2-CF3 | |
| II-198 | — | CH3 | CH3 | 3-pyridine | 2-CF3-6-Cl | |
| II-199 | — | CH3 | CH3 | 3-pyridine | 2-CH2OCH3 | |
| II-200 | — | CH3 | CH3 | 3-pyridine | 2-CH2OCH3-6-CH3 | |
| II-201 | — | CH3 | CH3 | 3-pyridine | 2-CH2OCH3-6-Cl | |
| II-202 | — | CH3 | CH3 | 3-pyridine | 2-CH2OCH3-6-SCH3 | |
| II-203 | — | CH3 | CH3 | 3-pyridine | 2-CH2SCH3 | |
| II-204 | — | CH3 | CH3 | 3-pyridine | 2-CH2SCH3-6-CH3 | |
| II-205 | — | CH3 | CH3 | 3-pyridine | 2-CH2SCH3-6-Cl | |
| II-206 | — | CH3 | CH3 | 3-pyridine | 2-CH2SO2CH3 | |
| II-207 | — | CH3 | CH3 | 3-pyridine | 2-CH2SO2CH3-6-CH3 | |
| II-208 | — | CH3 | CH3 | 3-pyridine | 2-CH2SO2CH3-6-Cl | |
| II-209 | — | CH3 | CH3 | 3-pyridine | 2-CH2SO2CH3-6-Cl | |
| II-210 | — | CH3 | CH3 | 3-pyridine | 2-CH3 | |
| II-211 | —(n = 0) | CH3 | CH3 | 3-pyridine | 2-CH3-6-CH2SCH3 | |
| II-212 | — | CH3 | CH3 | 3-pyridine | 2-CH3-6-CH2SCH3 | |
| II-213 | — | CH3 | CH3 | 3-pyridine | 2-CH3-6-CH3 | |
| II-214 | — | CH3 | CH3 | 3-pyridine | 2-CH3-6-Cl | |
| II-215 | — | CH3 | CH3 | 3-pyridine | 2-CH3-6-CN | |
| II-216 | — | CH3 | CH3 | 3-pyridine | 2-CH3-6-OCH3 | |
| II-217 | — | CH3 | CH3 | 3-pyridine | 2-CH3-6-SCH2Cl | |
| II-218 | — | CH3 | CH3 | 3-pyridine | 2-CH3-6-SCH2OCH3 | |
| II-219 | — | CH3 | CH3 | 3-pyridine | 2-CH3-6-SCH3 | |
| II-220 | — | CH3 | CH3 | 3-pyridine | 2-CH3-6-SO2CH2Cl | |
| II-221 | — | CH3 | CH3 | 3-pyridine | 2-CH3-6-SO2CH3 | |
| II-222 | — | CH3 | CH3 | 3-pyridine | 2-CN | |
| II-223 | — | CH3 | CH3 | 3-pyridine | 2-CN-6-CH3 | |
| II-224 | — | CH3 | CH3 | 3-pyridine | 2-CN-6-Cl | |
| II-225 | — | CH3 | CH3 | 3-pyridine | 2-CF3 | |
| II-226 | 1-CH3 | CH3 | CH3 | 3-pyridine | 2-CF3-6-Cl | |
| II-227 | 1-CH3 | CH3 | CH3 | 3-pyridine | 2-CH2OCH3 | |
| II-228 | 1-CH3 | CH3 | CH3 | 3-pyridine | 2-CH2OCH3-6-CH3 | |
| II-229 | 1-CH3 | CH3 | CH3 | 3-pyridine | 2-CH2OCH3-6-Cl | |
| II-230 | 1-CH3 | CH3 | CH3 | 3-pyridine | 2-CH2OCH3-6-SCH3 | |
| II-231 | 1-CH3 | CH3 | CH3 | 3-pyridine | 2-CH2SCH3 | |
| II-232 | 1-CH3 | CH3 | CH3 | 3-pyridine | 2-CH2SCH3-6-CH3 | |
| II-233 | 1-CH3 | CH3 | CH3 | 3-pyridine | 2-CH2SCH3-6-Cl | |
| II-234 | 1-CH3 | CH3 | CH3 | 3-pyridine | 2-CH2SO2CH3 | |
| II-235 | 1-CH3 | CH3 | CH3 | 3-pyridine | 2-CH2SO2CH3-6-CH3 | |

TABLE 2-continued

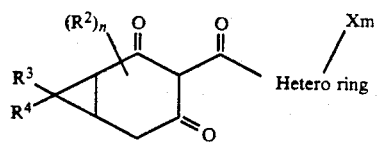

| No. | (R2)n | R3 | R4 | Hetero ring | Xm | Physical Properties |
|---|---|---|---|---|---|---|
| II-236 | 1-CH3 | CH3 | CH3 | 3-pyridine | 2-CH2SO2CH3-6-Cl | |
| II-237 | 1-CH3 | CH3 | CH3 | 3-pyridine | 2-CH2SO2CH3-6-Cl | |
| II-238 | 1-CH3 | CH3 | CH3 | 3-pyridine | 2-CH3 | |
| II-239 | 1-CH3 | CH3 | CH3 | 3-pyridine | 2-CH3-6-CH2SCH3 | |
| II-240 | 1-CH3 | CH3 | CH3 | 3-pyridine | 2-CH3-6-CH2SCH3 | |
| II-241 | 1-CH3 | CH3 | CH3 | 3-pyridine | 2-CH3-6-CH3 | |
| II-242 | 1-CH3 | CH3 | CH3 | 3-pyridine | 2-CH3-6-Cl | |
| II-243 | 1-CH3 | CH3 | CH3 | 3-pyridine | 2-CH3-6-CN | |
| II-244 | 1-CH3 | CH3 | CH3 | 3-pyridine | 2-CH3-6-OCH3 | |
| II-245 | 1-CH3 | CH3 | CH3 | 3-pyridine | 2-CH3-6-SCH2Cl | |
| II-246 | 1-CH3 | CH3 | CH3 | 3-pyridine | 2-CH3-6-SCH2OCH3 | |
| II-247 | 1-CH3 | CH3 | CH3 | 3-pyridine | 2-CH3-6-SCH3 | |
| II-248 | 1-CH3 | CH3 | CH3 | 3-pyridine | 2-CH3-6-SO2CH2Cl | |
| II-249 | 1-CH3 | CH3 | CH3 | 3-pyridine | 2-CH3-6-SO2CH3 | |
| II-250 | 1-CH3 | CH3 | CH3 | 3-pyridine | 2-CN | |
| II-251 | 1-CH3 | CH3 | CH3 | 3-pyridine | 2-CN-6-CH3 | |
| II-252 | 1-CH3 | CH3 | CH3 | 3-pyridine | 2-CN-6-Cl | |
| II-253 | —(n = 0) | H | H | 2-pyrimidine | 5-CF3 | |
| II-254 | — | H | H | 2-pyrimidine | 5-SCH3 | |
| II-255 | — | H | H | 2-pyrimidine | 5-SOCH3 | |
| II-256 | — | H | H | 2-pyrimidine | 5-SO2CH3 | |
| II-257 | — | H | H | 5-pyrimidine | 4-CH3-2-SCH3 | |
| II-258 | — | H | H | 5-pyrimidine | 4-CH3-2-OCH3 | |
| II-259 | — | H | H | 5-pyrimidine | 4-CH3-2-CH3 | |
| II-260 | — | H | H | 5-pyrimidine | 4-CH3-2-CF3 | |
| II-261 | — | H | H | 5-pyrimidine | 4-CH3-2-C2H5 | |
| II-262 | — | H | H | 5-pyrimidine | 4-OCH3-2-SCH3 | |
| II-263 | — | H | H | 5-pyrimidine | 4-OCH3-2-OCH3 | |
| II-264 | — | H | H | 5-pyrimidine | 4-OCH3-2-CH3 | |
| II-265 | — | H | H | 5-pyrimidine | 4-OCH3-2-CF3 | |
| II-266 | — | H | H | 5-pyrimidine | 4-OCH3-2-C2H5 | |
| II-267 | — | H | H | 5-pyrimidine | 4-SCH3-2-SCH3 | |
| II-268 | — | H | H | 5-pyrimidine | 4-SCH3-2-OCH3 | |
| II-269 | — | H | H | 5-pyrimidine | 4-SCH3-2-CH3 | |
| II-270 | — | H | H | 5-pyrimidine | 4-SCH3-2-CF3 | |
| II-271 | —(n = 0) | H | H | 5-pyrimidine | 4-SCH3-2-C2H5 | |
| II-272 | — | H | H | 5-pyrimidine | 4-CF3-2-SCH3 | |
| II-273 | — | H | H | 5-pyrimidine | 4-CF3-2-OCH3 | |
| II-274 | — | H | H | 5-pyrimidine | 4-CF3-2-CH3 | |
| II-275 | — | H | H | 5-pyrimidine | 4-CF3-2-CF3 | |
| II-276 | — | H | H | 5-pyrimidine | 4-CF3-2-C2H5 | |
| II-277 | 5-CH3 | H | H | 3-pyridine | 2-CH3-6-Cl | mp 93–6(cis) |
| II-278 | 5-CH3 | H | H | 5-thiazole | 2-OCH3-4-CH3 | powder(trans) |
| II-279 | 1-CH3 | H | H | 3-pyrazole | 1(N)-CH3-4-NO2 | mp 158–160 |

TABLE 3

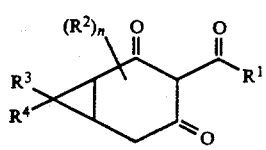

| No. | R1 | (R2)n | R3 | R4 | Physical Properties |
|---|---|---|---|---|---|
| III-1 | CH3 | 1,5,5-(CH3)3 | H | H | |
| III-2 | C2H5 | 1,5,5-(CH3)3 | H | H | |
| III-3 | C3H7 | 1,5,5-(CH3)3 | H | H | |
| III-4 | CH3 | 5,5-(CH3)2 | H | H | |
| III-5 | C2H5 | 5,5-(CH3)2 | H | H | |
| III-6 | C3H7 | 5,5-(CH3)2 | H | H | |
| III-7 | CH3 | 5-CH3 | H | H | |
| III-8 | C2H5 | 5-CH3 | H | H | |
| III-9 | C3H7 | 5-CH3 | H | H | |
| III-10 | CH3 | 1-CH3 | H | H | |
| III-11 | C2H5 | 1-CH3 | H | H | |
| III-12 | C3H7 | 1-CH3 | H | H | |

TABLE 3-continued

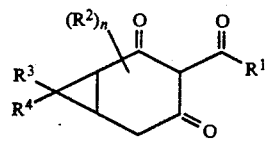

| No. | R1 | (R2)n | R3 | R4 | Physical Properties |
|---|---|---|---|---|---|
| III-13 | CH3 | —(n = 0) | H | H | nD 25.0 1.5489 |
| III-14 | C2H5 | — | H | H | |
| III-15 | C3H7 | — | H | H | nD 25.0 1.5260 |
| III-16 | CH3 | — | CH3 | CH3 | |
| III-17 | C2H5 | — | CH3 | CH3 | |
| III-18 | C3H7 | — | CH3 | CH3 | |
| III-19 | CH2Rx | — | H | H | nD 25.0 1.5810 |

As mentioned previously, the compounds possess superior herbicidal activity. The compounds may be applied directly to the soil as pre-emergence treatment or to plant foliage as post-emergence treatment, or they can be mixed intimately with soil. The compounds may be applied to soil or to plant foliage in amount of 1 g or more per 10 are.

A herbicidal composition having a compound of this invention as its active ingreadient may be formulated by mixing suitable carriers in a form generally used in agricultural chemicals such as wettable powder, water soluble powder, granule, emulsifiable concentrate and flowable. As solid carriers, talc, white carbon (silica), bentonite, clay, diatomaceous earth or the like may be used. As liquid carriers, water, alcohol, benzene, xylene, kerosene, mineral oil, cyclohexane, cyclohexanone, dimethylformamide or the like may be used. A surface active agent may, if necessary, be added in order to give a homogeneous and stable formulation.

Compounds can also be applied admixed with other chemicals, which are used in agronomic and horticultural management and which are compatible with such compounds. Such chemicals can be, but are not restricted to, the classes of chemical commonly known as fungicides, insecticides, acaricides, herbicides and plant growth regulators. In particular, by mixing it with the other herbicides, its applied dosage and manpower can be decreased and furthermore, the higher effect by synergetic function of both chemicals can be expected. For admixture of the compound with known herbicides, the use is recomended of benthiocarb, molinate, MY-93(S-(2,2-dimethylbenyil) 1-piperidinecarbothioate) or other carbamate-type herbicides; thiocarbamate-type herbicides; butachlor, pretilachlor, mefenacet or other acid amide-type herbicides; chlormethoxynil, bifenox or other diphenylether-type herbicides; atrazine, cyanazine or other triazine-type herbicides; chlorsulfurnon, sulfometuron-methyl or other sulfonylurea-type herbicides; MCP, MCPB or other phenoxy alkane carboxylic acid-type herbicides; diclofop-methyl or other phenoxy propionic acid-type herbicides; benzoyl-prop-ethyl, flamprop-ethyl or other benzoylaminopropionic acid-type herbicides; and, as others, piperophos, dymron, bentazon, difenzoquart, naproanilid, HW-52 (4-ethoxy methoxy benzo-2', 3'-dichloroanilide), KNW-242 (1-(3-methylphenyl)-5-phenyl-1H-1,2,4-triazole-3-carboxamide), quinclorac (3,7-dichloro-8-quinoline carboxylic acid), and further, sethoxydim, alloxydim-sodium and other cyclohexanedione-type herbicides. These herbicides in various combinations may also be mixed with a vegetable oil or an oil concentrate.

The concentration of the active ingredient in a herbicidal composition may vary according to type of formulation, and the concentration is, for example, in the range of 5-70 weight percent, preferably 10-30 weight percent, in wettable powder; 3-70 weight percent, preferably 5-20 weight percent, in emulsifiable concentrate; 0.01-30 weight percent, preferably 0.05-10 weight percent, in granule.

A wettable powder, or an emulsifiable concentrate thus produced may be diluted with water to a specified concentration and used as a liquid suspension or a liquid emulsion for treating soils or plant foliage. Further, a granule may be directly applied for soil or mixed with soil.

Non-limiting examples of herbicidal composition are illustrated by the following Examples:

EXAMPLE 3: Wettable powder

|  | parts by weight |
|---|---|
| Compound of this invention | 20 |
| White carbon | 20 |
| Diatomaceous earth | 52 |
| Sodium alkylsulfate | 8 |

These are mixed homogeneously and reduced to fine particles to provide a wettable powder containing 20% of active ingredient. In use, it is diluted to a desired concentration with water, and is sprayed as suspension.

EXAMPLE 4: Emulsifiable concentrate

|  | parts by weight |
|---|---|
| Compound of this invention | 20 |
| Xylene | 55 |
| dimethylformamide | 15 |
| Polyoxyethylene phenyl ether | 10 |

These are mixed and dissolved to provide an emulsifiable concentrate containing 20% of active ingredient. In use, it is diluted to a desired concentration with water, and sprayed as an emulsion.

EXAMPLE 5: Granule

|  | parts by weight |
|---|---|
| Compound of this invention | 5 |
| Talc | 40 |
| Clay | 38 |
| Bentonite | 10 |
| sodium alkyl sulfate | 7 |

These are mixed homogeneously to provide a granule containing 5% of active ingredient.

Industrial Applicability:

The herbicidal effects of compounds are illustrated by the following test:

Test 1: Postemergence treatment test

Seeds of Henry crabgrass, giant foxtail, rice flatsedge, velvetleaf, redroot pigweed and corn were planted in clay pots (200 cm$^2$) containing clay loam soil and were allowed to grow in greenhouse. When the plants were grown to a 5-10 cm height, aqueous suspensions, prepared by diluting an emulsifiable concentrate with water to specified concentration (250 ppm), were sprayed on the foliage of the plants at a rate of 100 1/10a by using a micro-sprayer.

Three weeds after treatment, the degree of damage of the each plants was observed and evaluated on the scale of value of 0-10, which has the following meanings.

| Index | Degree of damage |
|---|---|
| 0 | 0% |
| 2 | 20-29% |
| 4 | 40-40% |
| 6 | 60-69% |
| 8 | 80-89% |
| 10 | 100% |

Index 1,3,5,7 and 9 mean the intermediate degree between 0 and 2,2 and 4,4 and 6,6 and 8,8 and 10 respectively.

$$\text{Degree of damage (\%)} = \frac{\left(\begin{array}{c}\text{fresh weight in}\\\text{untreated plot}\end{array}\right) - \left(\begin{array}{c}\text{Fresh weight in}\\\text{treated plot}\end{array}\right)}{\text{Fresh weight in untreated plot}} \times 100$$

The results are shown in Table 4.

TABLE 4

| Compound No. | Henry carb-grass | giant foxtail | velvet-leaf | redroot pigweed | rice flat-sedge | corn |
|---|---|---|---|---|---|---|
| I-10 | 10 | 10 | 10 | 10 | 10 | 3 |
| I-20 | 10 | 10 | 10 | 10 | 10 | 0 |
| I-21 | 10 | 10 | 10 | 10 | 10 | 0 |
| I-35 | 10 | 10 | 10 | 10 | 10 | 0 |
| I-36 | 10 | 10 | 10 | 10 | 10 | 0 |
| I-48 | 10 | 10 | 10 | 10 | 10 | 1 |
| I-49 | 10 | 10 | 10 | 10 | 10 | 0 |
| I-50 | 10 | 10 | 10 | 10 | 10 | 0 |
| I-54 | 10 | 10 | 10 | 10 | 10 | 0 |
| I-55 | 10 | 10 | 10 | 10 | 10 | 1 |
| I-56 | 10 | 10 | 10 | 10 | 10 | 0 |
| I-57 | 10 | 10 | 10 | 10 | 10 | 0 |
| I-65 | 10 | 10 | 10 | 10 | 10 | 1 |
| I-81 | 10 | 10 | 10 | 10 | 10 | 0 |
| I-85 | 10 | 10 | 10 | 10 | 10 | 1 |
| I-97 | 10 | 10 | 10 | 10 | 10 | 2 |
| I-98 | 10 | 10 | 10 | 10 | 10 | 2 |
| I-99 | 10 | 10 | 10 | 10 | 10 | 0 |
| I-100 | 10 | 10 | 10 | 10 | 10 | 0 |
| I-101 | 10 | 10 | 10 | 10 | 10 | 3 |
| I-109 | 10 | 10 | 10 | 10 | 10 | 0 |
| I-133 | 10 | 10 | 10 | 10 | 10 | 0 |
| I-143 | 10 | 10 | 10 | 10 | 10 | 0 |
| I-144 | 10 | 10 | 10 | 10 | 10 | 1 |
| I-145 | 10 | 10 | 10 | 10 | 10 | 0 |
| I-146 | 10 | 10 | 10 | 10 | 10 | 0 |
| I-168 | 10 | 10 | 10 | 10 | 10 | 0 |
| I-169 | 10 | 10 | 10 | 10 | 10 | 0 |
| I-170 | 10 | 10 | 10 | 10 | 10 | 2 |
| I-172 | 10 | 10 | 10 | 10 | 10 | 0 |
| I-173 | 10 | 10 | 10 | 10 | 10 | 2 |
| I-176 | 10 | 10 | 10 | 10 | 10 | 0 |
| I-177 | 10 | 10 | 10 | 10 | 10 | 0 |
| I-178 | 10 | 10 | 10 | 10 | 10 | 0 |
| I-179 | 10 | 10 | 10 | 10 | 10 | 3 |
| I-180 | 10 | 10 | 10 | 10 | 10 | 2 |
| I-181 | 10 | 10 | 10 | 10 | 10 | 3 |
| I-183 | 10 | 10 | 10 | 10 | 10 | 3 |
| I-184 | 10 | 10 | 10 | 10 | 10 | 3 |
| I-185 | 10 | 10 | 10 | 10 | 10 | 0 |
| I-186 | 10 | 10 | 10 | 10 | 10 | 0 |
| I-187 | 10 | 10 | 10 | 10 | 10 | 2 |
| I-188 | 10 | 10 | 10 | 10 | 10 | 3 |
| I-189 | 10 | 10 | 10 | 10 | 10 | 0 |
| I-190 | 10 | 10 | 10 | 10 | 10 | 2 |
| I-191 | 10 | 10 | 10 | 10 | 10 | 0 |
| I-192 | 10 | 10 | 10 | 10 | 10 | 0 |
| I-193 | 10 | 10 | 10 | 10 | 10 | 0 |
| I-195 | 10 | 10 | 10 | 10 | 10 | 0 |
| I-196 | 10 | 10 | 10 | 10 | 10 | 0 |
| I-197 | 10 | 10 | 10 | 10 | 10 | 3 |
| I-198 | 10 | 10 | 10 | 10 | 10 | 0 |
| I-200 | 10 | 10 | 10 | 10 | 10 | 0 |
| I-201 | 10 | 10 | 10 | 10 | 10 | 0 |
| I-202 | 10 | 10 | 10 | 10 | 10 | 0 |
| I-203 | 10 | 10 | 10 | 10 | 10 | 0 |
| I-204 | 10 | 10 | 10 | 10 | 10 | 1 |
| I-205 | 10 | 10 | 10 | 10 | 10 | 1 |
| I-207 | 10 | 10 | 10 | 10 | 10 | 2 |
| I-208 | 10 | 10 | 10 | 10 | 10 | 0 |
| I-209 | 10 | 10 | 10 | 10 | 10 | 0 |
| I-210 | 10 | 10 | 10 | 10 | 10 | 2 |
| I-211 | 10 | 10 | 10 | 10 | 10 | 0 |
| I-212 | 10 | 10 | 10 | 10 | 10 | 2 |
| I-214 | 10 | 10 | 10 | 10 | 10 | 0 |
| I-215 | 10 | 10 | 10 | 10 | 10 | 3 |
| I-216 | 10 | 10 | 10 | 10 | 10 | 0 |
| I-217 | 10 | 10 | 10 | 10 | 10 | 0 |
| I-218 | 10 | 10 | 10 | 10 | 10 | 0 |
| I-219 | 10 | 10 | 10 | 10 | 10 | 0 |
| I-220 | 10 | 10 | 10 | 10 | 10 | 0 |
| I-222 | 10 | 10 | 10 | 10 | 10 | 0 |
| I-224 | 10 | 10 | 10 | 10 | 10 | 3 |
| I-225 | 10 | 10 | 10 | 10 | 10 | 3 |
| I-228 | 10 | 10 | 10 | 10 | 10 | 0 |
| I-229 | 10 | 10 | 10 | 10 | 10 | 0 |
| I-230 | 10 | 10 | 10 | 10 | 10 | 0 |
| I-231 | 10 | 10 | 10 | 10 | 10 | 0 |
| I-232 | 10 | 10 | 10 | 10 | 10 | 0 |
| I-233 | 10 | 10 | 10 | 10 | 10 | 0 |
| I-234 | 10 | 10 | 10 | 10 | 10 | 0 |
| I-237 | 10 | 10 | 10 | 10 | 10 | 3 |
| I-238 | 10 | 10 | 10 | 10 | 10 | 0 |
| I-240 | 10 | 10 | 10 | 10 | 10 | 0 |
| I-241 | 10 | 10 | 10 | 10 | 10 | 0 |
| I-244 | 10 | 10 | 10 | 10 | 10 | 2 |
| I-245 | 10 | 10 | 10 | 10 | 10 | 2 |
| I-249 | 10 | 10 | 10 | 10 | 10 | 3 |
| I-250 | 10 | 10 | 10 | 10 | 10 | 0 |
| I-251 | 10 | 10 | 10 | 10 | 10 | 0 |
| I-254 | 10 | 10 | 10 | 10 | 10 | 0 |
| II-102 | 10 | 10 | 10 | 10 | 10 | 3 |
| II-109 | 10 | 10 | 10 | 10 | 10 | 0 |
| II-130 | 10 | 10 | 10 | 10 | 10 | 0 |
| II-137 | 10 | 10 | 10 | 10 | 10 | 0 |
| II-277 | 10 | 10 | 10 | 10 | 10 | 3 |
| Comparative Compound A | 6 | 7 | 8 | 4 | 5 | 7 |
| Comparative Compound B | 6 | 5 | 8 | 2 | 8 | 6 |

We claim:

1. A compound or an optical isomer or salt thereof represented by the formula I:

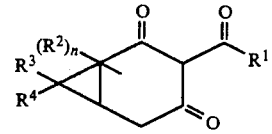

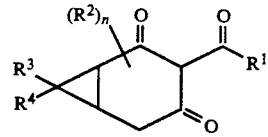

wherein, $R^1$ is (a) $C_{1-5}$ alkyl;
  (b) phenyl optionally substituted with
    (i) halogen,
    (ii) $C_{1-6}$ alkoxy
    (iii) $C_{1-4}$ alkyl,
    (iv) $C_{1-4}$ haloalkye,
    (v) $C_{1-4}$ alkylsulfonyl,
    (vi) $C_{1-4}$ alkoxy-$C_{1-4}$ alkyl,
    (vii) $C_{1-4}$ alkylthio-$C_{1-4}$ alkylthio,
    (viii) $C_{1-4}$ alkylthio,
    (ix) $C_{1-4}$ alkoxy-$C_{1-4}$ alkylthio,
    (x) nitro,
    (xi) $C_{1-4}$ alkylcarbonylamino,
    (xii) $C_{1-4}$ alkylthio-$C_{1-4}$ alkoxy,
    (xiii) $C_{2-4}$ alkenyloxy,
    (xiv) $C_{2-4}$ alkynyloxy,
    (xv) $C_{1-4}$ haloalkoxy, (xvi) $C_{1-4}$ dialkylaminosulfonyl,
(xvii) $C_{2-4}$ alkenylthio,
(xviii) $C_{1-4}$ haloalkylsulfonyl,
(xix) $C_{2-4}$ haloalkenyloxy,
(xx) $C_{1-4}$ alkylcarbonyl,
(xxi) $C_{1-4}$ alkoxy-$C_{1-4}$ alkylsulfonyl,
(xxii) $C_{1-4}$ alkoxy-$C_{1-4}$ alkoxy,
(xxiii) hydroxy,
(xxiv) halophenoxy, or,
(xxv) benzyloxy,
(c) benzyl group optionally substituted with halogen; or,
(d) pyridyl group optionally substituted with
(i) $C_{1-4}$ alkyl,
(ii) halogen, or
(iii) $C_{1-4}$ alkylsulfonyl,
$R^2$ is (a) halogen,
(b) $C_{1-4}$ alkoxy,
(c) $C_{1-4}$ alkylthio,
(d) $C_{1-4}$ alkylsulfonyl,
(e) $C_{1-4}$ alkyl,
(f) $C_{1-4}$ alkoxyalkyl, or,
(g) $C_{1-4}$ alkoxylcarbonyl;

n is an integer from 0 to 4; and,
$R^3$ and $R^4$ may be the same or different and each is
(a) hydrogen, or,
(b) $C_{1-3}$ alkyl.

2. A herbicidal composition comprising a herbicidally effective amount of a compound according to claim 1.

3. A method of controlling weed pests and protecting corn plants which comprises adding to the habitat thereof an herbicidally effective amount of the composition according to claim 2 in a herbicidally acceptable carrier.

4. The compound 3-(2-nitro-4-chlorobenzoyl) bicyclo heptane-2,4-dione.

5. The compound 3-(2-chloro-4-methylsulfonyl-3-methoxybenzoyl)-cis-5-methyl-cis-bicyclo -heptane-2,4-dione.

6. A herbicidal composition comprising a herbicidally effective amount of the compound of claim 4 and a herbicidally acceptable carrier.

7. A herbicidal composition comprising a herbicidally effective amount of the compound of claim 5 and a herbicidally acceptable carrier.

* * * * *